United States Patent
Farritor et al.

(10) Patent No.: US 11,701,193 B2
(45) Date of Patent: *Jul. 18, 2023

(54) USER CONTROLLER WITH USER PRESENCE DETECTION AND RELATED SYSTEMS AND METHODS

(71) Applicant: Virtual Incision Corporation, Lincoln, NE (US)

(72) Inventors: Shane Farritor, Lincoln, NE (US); Nathan Wood, Lincoln, NE (US); Jason Dumpert, Omaha, NE (US)

(73) Assignee: Virtual Incision Corporation, Lincoln, NE (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/706,893

(22) Filed: Mar. 29, 2022

(65) Prior Publication Data

US 2022/0218430 A1  Jul. 14, 2022

Related U.S. Application Data

(63) Continuation of application No. 16/896,678, filed on Jun. 9, 2020, now Pat. No. 11,284,958, which is a
(Continued)

(51) Int. Cl.
*A61B 34/30* (2016.01)
*A61B 34/00* (2016.01)
(Continued)

(52) U.S. Cl.
CPC ............. *A61B 34/74* (2016.02); *A61B 34/30* (2016.02); *A61B 34/77* (2016.02); *B25J 9/161* (2013.01);
(Continued)

(58) Field of Classification Search
CPC ......... A61B 34/74; A61B 34/30; A61B 34/77; A61B 2034/741; B25J 9/161; G05G 9/04737; G05G 5/005; G05G 2009/04774
See application file for complete search history.

(56) References Cited

U.S. PATENT DOCUMENTS

| 5,307,447 A | 4/1994 | Asano et al. |
| 5,388,528 A | 2/1995 | Pelrine et al. |

(Continued)

FOREIGN PATENT DOCUMENTS

| CN | 113017841 A | 6/2021 |
| CN | 113017841 A1 | 6/2021 |

(Continued)

OTHER PUBLICATIONS

Abbott et al., "Design of an Endoluminal NOTES Robotic System," from the Proceedings of the 2007 IEEE/RSJ Int'l Conf. on Intelligent Robot Systems, San Diego, CA, Oct. 29-Nov. 2, 2007, pp. 410-416.

(Continued)

*Primary Examiner* — Thomas C Diaz
(74) *Attorney, Agent, or Firm* — Fredrikson & Byron, P.A.

(57) ABSTRACT

The present invention is relates to a user controller having a thumb sheath with an open side defined in the thumb sheath. Further embodiments relate to thumb presence sensors and sensory feedback components associated with the thumb sheath. Additional embodiments relate to an adjustable thumb sheath. Still other embodiments relate to systems comprising such user controllers.

22 Claims, 13 Drawing Sheets

Related U.S. Application Data continuation of application No. 15/826,166, filed on Nov. 29, 2017, now Pat. No. 10,675,110.

(60) Provisional application No. 62/427,357, filed on Nov. 29, 2016.

(51) Int. Cl.
  *G05G 9/047* (2006.01)
  *B25J 9/16* (2006.01)
  *G05G 5/00* (2006.01)

(52) U.S. Cl.
  CPC .... *G05G 9/04737* (2013.01); *A61B 2034/741* (2016.02); *G05G 5/005* (2013.01); *G05G 2009/04774* (2013.01)

(56) References Cited

U.S. PATENT DOCUMENTS

| | | |
|---|---|---|
| 5,624,398 A | 4/1997 | Smith et al. |
| 5,657,429 A | 8/1997 | Wang et al. |
| 5,762,458 A | 6/1998 | Wang et al. |
| 5,791,231 A | 8/1998 | Cohn et al. |
| 5,825,982 A | 10/1998 | Wright et al. |
| 5,855,583 A | 1/1999 | Wang et al. |
| 5,876,325 A | 3/1999 | Mizuno et al. |
| 6,001,108 A | 12/1999 | Wang et al. |
| 6,223,100 B1 | 4/2001 | Green |
| 6,240,312 B1 | 5/2001 | Alfano et al. |
| 6,246,200 B1 | 6/2001 | Blumenkranz et al. |
| 6,296,635 B1 | 10/2001 | Smith et al. |
| 6,309,397 B1 | 10/2001 | Julian et al. |
| 6,312,435 B1 | 11/2001 | Wallace et al. |
| 6,331,181 B1 | 12/2001 | Tierney et al. |
| 6,364,888 B1 | 4/2002 | Niemeyer et al. |
| 6,398,726 B1 | 6/2002 | Ramans et al. |
| 6,424,885 B1 | 7/2002 | Niemeyer et al. |
| 6,436,107 B1 | 8/2002 | Wang et al. |
| 6,441,577 B2 | 8/2002 | Blumenkranz et al. |
| 6,450,104 B1 | 9/2002 | Grant et al. |
| 6,451,027 B1 | 9/2002 | Cooper et al. |
| 6,459,926 B1 | 10/2002 | Nowlin et al. |
| 6,463,361 B1 | 10/2002 | Wang et al. |
| 6,468,265 B1 | 10/2002 | Evans et al. |
| 6,470,236 B2 | 10/2002 | Ohtsuki |
| 6,491,701 B2 | 12/2002 | Nemeyer et al. |
| 6,493,608 B1 | 12/2002 | Niemeyer et al. |
| 6,522,906 B1 | 2/2003 | Salisbury, Jr. et al. |
| 6,544,276 B1 | 4/2003 | Azizi |
| 6,565,554 B1 | 5/2003 | Niemeyer |
| 6,574,355 B2 | 6/2003 | Green |
| 6,587,750 B2 | 7/2003 | Gerbi et al. |
| 6,594,552 B1 | 7/2003 | Nowlin et al. |
| 6,620,173 B2 | 9/2003 | Gerbi et al. |
| 6,645,196 B1 | 11/2003 | Nixon et al. |
| 6,659,939 B2 | 12/2003 | Moll et al. |
| 6,671,581 B2 | 12/2003 | Niemeyer et al. |
| 6,684,129 B2 | 1/2004 | Salisbury, Jr. et al. |
| 6,699,177 B1 | 3/2004 | Wang et al. |
| 6,714,839 B2 | 3/2004 | Salisbury, Jr. et al. |
| 6,714,841 B1 | 3/2004 | Wright et al. |
| 6,728,599 B2 | 4/2004 | Wright et al. |
| 6,764,445 B2 | 7/2004 | Ramans et al. |
| 6,766,204 B2 | 7/2004 | Niemeyer et al. |
| 6,770,081 B1 | 8/2004 | Cooper et al. |
| 6,783,524 B2 | 8/2004 | Anderson et al. |
| 6,785,593 B2 | 8/2004 | Wang et al. |
| 6,793,653 B2 | 9/2004 | Sanchez et al. |
| 6,799,065 B1 | 9/2004 | Niemeyer |
| 6,817,972 B2 | 11/2004 | Snow |
| 6,837,883 B2 | 1/2005 | Moll et al. |
| 6,839,612 B2 | 1/2005 | Sanchez et al. |
| 6,852,107 B2 | 2/2005 | Wang et al. |
| 6,858,003 B2 | 2/2005 | Evans et al. |
| 6,879,880 B2 | 4/2005 | Nowlin et al. |
| 6,899,705 B2 | 5/2005 | Niemeyer |
| 6,905,460 B2 | 6/2005 | Wang et al. |
| 6,905,491 B1 | 6/2005 | Wang et al. |
| 6,936,001 B1 | 8/2005 | Snow |
| 6,951,535 B2 | 10/2005 | Ghodoussi et al. |
| 6,965,812 B2 | 11/2005 | Wang et al. |
| 6,974,449 B2 | 12/2005 | Niemeyer |
| 6,994,703 B2 | 2/2006 | Wang et al. |
| 7,025,064 B2 | 4/2006 | Wang et al. |
| 7,027,892 B2 | 4/2006 | Wang et al. |
| 7,048,745 B2 | 5/2006 | Tierney et al. |
| 7,074,179 B2 | 7/2006 | Wang et al. |
| 7,083,571 B2 | 8/2006 | Wang et al. |
| 7,083,615 B2 | 8/2006 | Peterson et al. |
| 7,118,582 B1 | 10/2006 | Wang et al. |
| 7,121,781 B2 | 10/2006 | Sanchez et al. |
| 7,125,403 B2 | 10/2006 | Julian et al. |
| 7,126,303 B2 | 10/2006 | Farritor et al. |
| 7,155,315 B2 | 12/2006 | Niemeyer et al. |
| 7,169,141 B2 | 1/2007 | Brock et al. |
| 7,199,545 B2 | 4/2007 | Oleynikov et al. |
| 7,217,240 B2 | 5/2007 | Snow |
| 7,239,940 B2 | 7/2007 | Wang et al. |
| 7,372,229 B2 | 5/2008 | Farritor et al. |
| 7,492,116 B2 | 2/2009 | Oleynikov et al. |
| 7,574,250 B2 | 8/2009 | Niemeyer |
| 7,772,796 B2 | 8/2010 | Farritor et al. |
| 7,789,825 B2 | 9/2010 | Nobis et al. |
| 7,865,266 B2 | 1/2011 | Moll et al. |
| 7,960,935 B2 | 6/2011 | Farritor et al. |
| 8,179,073 B2 | 5/2012 | Farritor et al. |
| 8,343,171 B2 | 1/2013 | Farritor et al. |
| 8,679,096 B2 | 3/2014 | Farritor et al. |
| 8,828,024 B2 | 9/2014 | Farritor et al. |
| 8,834,488 B2 | 9/2014 | Farritor et al. |
| 8,894,633 B2 | 11/2014 | Farritor et al. |
| 8,968,267 B2 | 3/2015 | Nelson et al. |
| 8,968,332 B2 | 3/2015 | Farritor et al. |
| 8,974,440 B2 | 3/2015 | Farritor et al. |
| 9,010,214 B2 | 4/2015 | Markvicka et al. |
| 9,020,644 B2 | 4/2015 | Greeley et al. |
| 9,060,781 B2 | 6/2015 | Farritor et al. |
| 9,089,353 B2 | 7/2015 | Farritor et al. |
| 9,117,129 B1 | 8/2015 | Koch |
| 9,179,981 B2 | 11/2015 | Farritor et al. |
| 9,498,292 B2 | 11/2016 | Mondry et al. |
| 9,579,088 B2 | 2/2017 | Farritor et al. |
| 9,743,987 B2 | 8/2017 | Farritor et al. |
| 9,757,187 B2 | 9/2017 | Farritor et al. |
| 9,770,305 B2 | 9/2017 | Farritor et al. |
| 9,883,911 B2 | 2/2018 | Farritor et al. |
| 9,888,966 B2 | 2/2018 | Farritor et al. |
| 9,956,043 B2 | 5/2018 | Farritor et al. |
| 10,111,711 B2 | 10/2018 | Farritor et al. |
| 10,219,870 B2 | 3/2019 | Mondry et al. |
| 10,307,199 B2 | 6/2019 | Farritor et al. |
| 10,335,024 B2 | 7/2019 | Rentschler et al. |
| 10,342,561 B2 | 7/2019 | Farritor et al. |
| 10,376,322 B2 | 8/2019 | Frederick et al. |
| 10,470,828 B2 | 11/2019 | Markvicka et al. |
| 10,582,973 B2 | 3/2020 | Wilson et al. |
| 10,667,883 B2 | 6/2020 | Farritor et al. |
| 10,702,347 B2 | 7/2020 | Farritor et al. |
| 10,751,136 B2 | 8/2020 | Farritor et al. |
| 10,806,538 B2 | 10/2020 | Farritor et al. |
| 10,966,700 B2 | 4/2021 | Farritor et al. |
| 11,284,958 B2 * | 3/2022 | Farritor ................ A61B 34/30 |
| 2002/0091374 A1 | 6/2002 | Cooper |
| 2002/0120254 A1 | 8/2002 | Julian et al. |
| 2002/0128552 A1 | 9/2002 | Nowlin et al. |
| 2002/0171385 A1 | 11/2002 | Kim et al. |
| 2003/0020810 A1 | 1/2003 | Takizawa et al. |
| 2003/0100817 A1 | 5/2003 | Wang et al. |
| 2003/0135203 A1 | 6/2003 | Wang et al. |
| 2004/0024311 A1 | 2/2004 | Quaid |
| 2004/0106916 A1 | 6/2004 | Quaid et al. |
| 2004/0254680 A1 | 12/2004 | Sunaoshi |
| 2005/0064378 A1 | 3/2005 | Toly |
| 2006/0119304 A1 | 6/2006 | Farritor et al. |

(56) References Cited

U.S. PATENT DOCUMENTS

| | | |
|---|---|---|
| 2006/0155263 A1 | 7/2006 | Lipow |
| 2006/0241570 A1 | 10/2006 | Wilk |
| 2006/0253109 A1 | 11/2006 | Chu |
| 2007/0156019 A1 | 7/2007 | Larkin et al. |
| 2008/0004634 A1 | 1/2008 | Farritor et al. |
| 2008/0058835 A1 | 3/2008 | Farritor et al. |
| 2008/0111513 A1 | 5/2008 | Farritor et al. |
| 2008/0221591 A1 | 9/2008 | Farritor et al. |
| 2009/0024142 A1 | 1/2009 | Ruiz Morales |
| 2009/0048612 A1 | 2/2009 | Farritor et al. |
| 2009/0054909 A1 | 2/2009 | Farritor et al. |
| 2009/0069821 A1 | 3/2009 | Farritor et al. |
| 2009/0076536 A1 | 3/2009 | Rentschler et al. |
| 2009/0137952 A1 | 5/2009 | Ramamurthy et al. |
| 2009/0163929 A1 | 6/2009 | Yeung et al. |
| 2009/0240246 A1 | 9/2009 | Devill et al. |
| 2009/0248038 A1 | 10/2009 | Blumenkranz et al. |
| 2009/0281377 A1 | 11/2009 | Newell et al. |
| 2009/0305210 A1 | 12/2009 | Guru et al. |
| 2010/0010294 A1 | 1/2010 | Conlon et al. |
| 2010/0042097 A1 | 2/2010 | Newton et al. |
| 2010/0139436 A1 | 6/2010 | Kawashima et al. |
| 2010/0262162 A1 | 10/2010 | Omori |
| 2010/0318059 A1 | 12/2010 | Farritor et al. |
| 2011/0071347 A1 | 3/2011 | Rogers et al. |
| 2011/0071544 A1 | 3/2011 | Steger et al. |
| 2011/0224605 A1 | 9/2011 | Farritor et al. |
| 2011/0237890 A1 | 9/2011 | Farritor et al. |
| 2011/0238080 A1 | 9/2011 | Ranjit et al. |
| 2011/0264078 A1 | 10/2011 | Lipow et al. |
| 2012/0041595 A1 | 2/2012 | Greeley et al. |
| 2012/0109150 A1 | 5/2012 | Quaid et al. |
| 2012/0179168 A1 | 7/2012 | Farritor et al. |
| 2012/0253515 A1 | 10/2012 | Coste-Maniere et al. |
| 2013/0197697 A1 | 8/2013 | Schaible et al. |
| 2013/0345717 A1 | 12/2013 | Markvicka et al. |
| 2014/0039515 A1 | 2/2014 | Mondry et al. |
| 2014/0046340 A1 | 2/2014 | Wilson et al. |
| 2014/0058205 A1 | 2/2014 | Frederick et al. |
| 2014/0303434 A1 | 10/2014 | Farritor et al. |
| 2015/0051446 A1 | 2/2015 | Farritor et al. |
| 2015/0190170 A1 | 7/2015 | Frederick et al. |
| 2018/0168758 A1* | 6/2018 | Lutzow ............... A61B 34/37 |

FOREIGN PATENT DOCUMENTS

| | | |
|---|---|---|
| EP | 2286756 | 2/2011 |
| JP | 08224248 | 9/1996 |
| JP | 2004180781 | 7/2004 |
| JP | 2009106606 | 5/2009 |
| JP | 2010533045 | 10/2010 |
| JP | 2010536436 | 12/2010 |
| JP | 2011045500 | 3/2011 |
| WO | 2002082979 | 10/2002 |
| WO | 2006079108 | 7/2006 |
| WO | 2007149559 | 12/2007 |
| WO | 2009023851 | 2/2009 |
| WO | 2010050771 | 5/2010 |
| WO | 2011060187 A1 | 5/2011 |
| WO | 2011075693 | 6/2011 |
| WO | 2013009887 | 1/2013 |
| WO | 2014011238 | 1/2014 |
| WO | 2016114090 A1 | 7/2016 |
| WO | 2016126334 A1 | 8/2016 |
| WO | 2016201544 A1 | 12/2016 |

OTHER PUBLICATIONS

Ballantyne, "Robotic Surgery, Telerobotic Surgery, Telepresence, and Telementoring," Surgical Endoscopy, 2002; 16: 1389-1402.

Bauer et al., "Case Report: Remote Percutaneous Renal Percutaneous Renal Access Using a New Automated Telesurgical Robotic System," Telemedicine Journal and e-Health 2001; (4): 341-347.

Berg et al., "Surgery with Cooperative Robots," Medicine Meets Virtual Reality, Feb. 2007, 1 pg.

Camarillo et al., "Robotic Technology in Surgery: Past, Present and Future," The American Journal of Surgery, 2004; 188: 2S-15.

Cavusoglu et al., "Telesurgery and Surgical Simulation: Haptic Interfaces to Real and Virtual Surgical Environments," In McLaughliin, M.L., Hespanha, J.P., and Sukhatme, G., editors. Touch in virtual environments, IMSC Series in Multimedia 2001, 28pp.

Green, "Telepresence Surgery", Jan. 1, 1995, Publisher: IEEE Engineering in Medicine and Biology.

Cleary et al., "State of the Art in Surgical Rooties: Clinical Applications and Technology Challenges", "Computer Aided Surgery", Jan. 1, 2002, pp. 312-328, vol. 6.

Stoianovici et al., "Robotic Tools for Minimally Invasive Urologic Surgery", Jan. 1, 2002, pp. 1-17.

Franzino, "The Laprotek Surgical System and the Next Generation of Robotics," Surg Clin North Am, 2003 83(6): 1317-1320.

Falcone et al., "Robotic Surgery," Clin. Obstet. Gynecol. 2003, 46(1): 37-13.

Fraulob et al., "Miniature assistance module for robot-assisted heart surgery," Biomed. Tech. 2002, 47 Suppl. 1, Pt. 1: 12-15.

Dakin et al., "Comparison of laparoscopic skills performance between standard instruments and two surgical robotic systems," Surg Endosc., 2003; 17: 574-579.

Cavusoglu et al., "Robotics for Telesurgery: Second Generation Berkeley/UCSF Laparoscopic Telesurgical Workstation and Looking Towards the Future Applications," Industrial Robot: An International Journal, 2003; 30(1):22-29.

* cited by examiner

USER CONTROLLER WITH USER PRESENCE DETECTION AND RELATED SYSTEMS AND METHODS

CROSS-REFERENCE TO RELATED APPLICATION(S)

This application claims priority as a continuation application to U.S. patent application Ser. No. 16/896,678, filed Jun. 9, 2020 and entitled "User Controller with User Presence Detection and Related Systems and Methods," which issued as U.S. Pat. No. 11,284,958 on Mar. 29, 2022, which claims priority as a continuation to U.S. patent application Ser. No. 15/826,166, filed Nov. 29, 2017, and entitled "User Controller with User Presence Detection and Related Systems and Methods," which issued as U.S. Pat. No. 10,675,110 on Jun. 9, 2020, which claims priority to U.S. Provisional Application 62/427,357, filed Nov. 29, 2016, and entitled "Controller with User Presence Detection and Related Systems and Methods," all of which are hereby incorporated herein by reference in their entireties.

FIELD OF THE INVENTION

The various embodiments herein relate to user presence detection on a multi-degree-of-freedom (DOF) user input device for use in systems such as, for example, robotic medical device systems.

BACKGROUND OF THE INVENTION

User input devices with many degrees of freedom require the user to support the mass of the input device.

One example of such a known input device is depicted in FIGS. 1-2B. FIG. 1 depicts the multi-DOF user input device 8 for the left hand of the user. To interface with the device 8, the user places the left palm on the main body 10 of the user controller 8, the forefinger on the forefinger interface 12 that is able to move relative to the main body 10 via a rotary link 14, and the thumb in the thumb groove 16. The main body 10 of the user interface 8 is connected to a multi-DOF positioning or sensing system through a linkage 18. In order to supply forces and torques to move the user interface 8 both a thumb restraint 20 and forefinger restraint 22 to constrain the users hand to the device 8.

FIGS. 2A and 2B depict the ability of the user to further input an open/close motion of the forefinger interface 12, which is connected to the main body 10 using a link 14 and rotary joint 30. The minimum displacement 32 (as shown in FIG. 2A) and maximum displacement 34 (as shown in FIG. 2B) can be measured and used as an additional control signal. The thumb restraint 20 and forefinger restraint 22 supply constraints such that the user maintains control of the main body 10 while moving the grasper throughout its range of motion. Such restraints, while enabling the user to input another control signal, make it difficult for the user to disengage with the device 8 in a controlled manner.

Further, in order for the user to exit the device in a controlled fashion, support of the input device must transferred to the input device itself or the signal being output by the device must cease. That is, during use, the input device is supported or maintained in its operable position by the hand of the user, but removal of the user's hand from the input device without any mechanical force applied by the system itself causes the input device to be pulled downward by gravity, which can result in the robotic device or component operably coupled to the input device to move or be actuated in an undesirable fashion.

There is a need in the art for improved methods and devices for detecting the presence of a user at, on, or using a user input device.

BRIEF SUMMARY OF THE INVENTION

Discussed herein are various user controllers for use with various systems, including robotic surgical systems.

In Example 1, a user controller comprises a controller body and a thumb sheath coupled to the controller body. The thumb sheath comprises a first sheath section extending from the controller body, and a second sheath section extending from the first sheath section, wherein the second sheath section is transverse to the first sheath segment. The first sheath section, the second sheath section, and the controller body define a thumb opening and an open side.

Example 2 relates to the user controller according to Example 1, wherein the first sheath section, the second sheath section, and the controller body do not form a 360° enclosure around the thumb opening.

Example 3 relates to the user controller according to Example 1, further comprising a light sensor disposed within the thumb opening.

Example 4 relates to the user controller according to Example 1, further comprising a light emitter disposed on an inner wall of the thumb sheath and a light receiver disposed on the controller body, wherein the light receiver is positioned to receive light transmitted by the light emitter.

Example 5 relates to the user controller according to Example 1, further comprising a light emitter disposed on the controller body and a light receiver disposed on an inner wall of the thumb sheath, wherein the light receiver is positioned to receive light transmitted by the light emitter.

Example 6 relates to the user controller according to Example 1, further comprising a light emitter and a light receiver, wherein the light emitter and light receiver are disposed on the controller body.

Example 7 relates to the user controller according to Example 1, further comprising a capacitive sensor disposed on the controller body within the thumb sheath.

Example 8 relates to the user controller according to Example 1, further comprising a mechanical sensor disposed on the controller body within the thumb sheath.

Example 9 relates to the user controller according to Example 1, wherein the thumb sheath is adjustable between a retracted position and an extended position.

Example 10 relates to the user controller according to Example 1, further comprising a feedback signal component disposed on an outer surface of the thumb sheath, wherein the feedback signal component is visible to a user.

Example 11 relates to the user controller according to Example 1, wherein a user's thumb is removable from the thumb sheath via the thumb opening or the open side.

In Example 12, a robotic surgical system comprises a system controller, a robotic surgical device operably coupled to the system controller, and a user controller operably coupled to the system controller. The robotic surgical device comprises a device body, at least one robotic arm operably coupled to the device body, and at least one end effector operably coupled to the robotic arm. The user controller comprises a controller body, and a thumb sheath coupled to the controller body, wherein the thumb sheath and the controller body define a thumb opening and a side opening.

Example 13 relates to the robotic surgical system according to Example 12, wherein the thumb sheath comprises a first sheath section extending from the controller body and defining a first wall of the thumb opening, a second sheath section extending from the first sheath second and defining a second wall of the thumb opening, and a third wall of the thumb opening defined by the controller body.

Example 14 relates to the robotic surgical system according to Example 13, wherein the side opening is defined between the second wall and the third wall.

Example 15 relates to the robotic surgical system according to Example 12, wherein the thumb sheath does not form a 360° enclosure around the thumb opening.

Example 16 relates to the robotic surgical system according to Example 12, further comprising a thumb presence sensor disposed within the thumb opening.

Example 17 relates to the robotic surgical system according to Example 16, wherein the thumb presence sensor comprises a light sensor, a capacitive sensor, or a mechanical sensor.

Example 18 relates to the robotic surgical system according to Example 12, wherein the thumb sheath is adjustable between a retracted position and an extended position.

Example 19 relates to the robotic surgical system according to Example 12, further comprising a feedback signal component disposed on an outer surface of the thumb sheath, wherein the feedback signal component is visible to a user.

Example 20 relates to the robotic surgical system according to Example 12, wherein a user's thumb is removable from the thumb sheath via the thumb opening or the side opening.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

DETAILED DESCRIPTION

Figure 1:
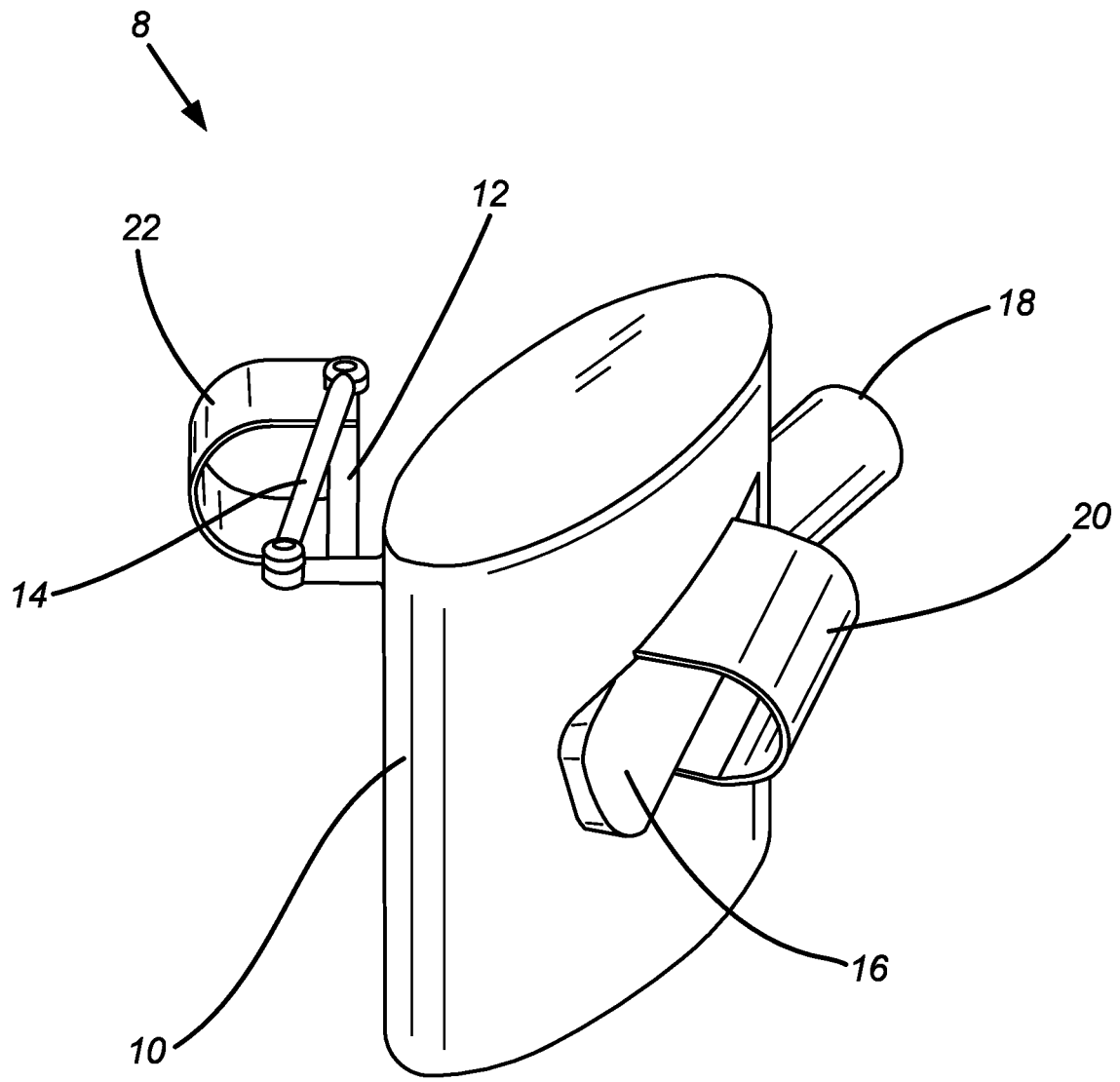
FIG. 1 is a perspective view of a known user input device.

The various embodiments herein relate to methods and devices for detecting the presence of a user at, on, or using a multi-DOF user input device in which the user grasps the device using a pincer grasp. That is, the various embodiments have a sheath mounted on the input device that is configured to detect the presence of the user's hand. If the user's hand (or more specifically the thumb, according to certain embodiments) is detected by the sheath, the device transmits a signal ("the presence signal") to the system (such as, for example, the system controller component of the system) that the user is in position and control should be enabled. When the hand is removed, the absence of the "presence signal" can be used to cease use of the device output or, if it is haptically enabled, lock the device in place.

It is understood that the various user controller embodiments herein can be used with various robotic surgical systems in which the user controller is the user interface and is coupled to the surgical system such that the user controller can be used to control a robotic surgical device positioned into or within a cavity of a patient. That is, the various user controller embodiments and related systems and methods disclosed herein can be incorporated into, used in conjunction with, or used as part of any other known robotic surgical systems, devices, or methods. For example, the various embodiments disclosed herein may be incorporated into or used with any of the medical devices and systems disclosed in U.S. Pat. No. 8,968,332 (issued on Mar. 3, 2015 and entitled "Magnetically Coupleable Robotic Devices and Related Methods"), U.S. Pat. No. 8,834,488 (issued on Sep. 16, 2014 and entitled "Magnetically Coupleable Surgical Robotic Devices and Related Methods"), U.S. patent application Ser. No. 14/617,232 (filed on Feb. 9, 2015 and entitled "Robotic Surgical Devices and Related Methods"), U.S. Pat. No. 9,579,088 (issued on Feb. 28, 2017 and entitled "Methods, Systems, and Devices for Surgical Visualization and Device Manipulation"), U.S. Pat. No. 8,343,171 (issued on Jan. 1, 2013 and entitled "Methods and Systems of Actuation in Robotic Devices"), U.S. Pat. No. 8,828,024 (issued on Sep. 9, 2014 and entitled "Methods and Systems of Actuation in Robotic Devices"), U.S. patent application Ser. No. 14/454,035 (filed Aug. 7, 2014 and entitled "Methods and Systems of Actuation in Robotic Devices"), U.S. patent application Ser. No. 12/192,663 (filed Aug. 15, 2008 and entitled Medical Inflation, Attachment, and Delivery Devices and Related Methods"), U.S. patent application Ser. No. 15/018,530 (filed Feb. 8, 2016 and entitled "Medical Inflation, Attachment, and Delivery Devices and Related Methods"), U.S. Pat. No. 8,974,440 (issued on Mar. 10, 2015 and entitled "Modular and Cooperative Medical Devices and Related Systems and Methods"), U.S. Pat. No. 8,679,096 (issued on Mar. 25, 2014 and entitled "Multifunctional Operational Component for Robotic Devices"), U.S. Pat. No. 9,179,981 (issued on Nov. 10, 2015 and entitled "Multifunctional Operational Component for Robotic Devices"), U.S. patent application Ser. No. 14/936,234 (filed on Nov. 9, 2015 and entitled "Multifunctional Operational Component for Robotic Devices"), U.S. Pat. No. 8,894,633 (issued on Nov. 25, 2014 and entitled "Modular and Cooperative Medical Devices and Related Systems and Methods"), U.S. Pat. No. 8,968,267 (issued on Mar. 3, 2015 and entitled "Methods and Systems for Handling or Delivering Materials for Natural Orifice Surgery"), U.S. Pat. No. 9,060,781 (issued on Jun. 23, 2015 and entitled "Methods, Systems, and Devices Relating to Surgical End Effectors"), U.S. patent application Ser. No. 14/745,587 (filed on Jun. 22, 2015 and entitled "Methods, Systems, and Devices Relating to Surgical End Effectors"), U.S. Pat. No. 9,089,353 (issued on Jul. 28, 2015 and entitled "Robotic Surgical Devices, Systems, and Related Methods"), U.S. patent application Ser. No. 14/800,423 (filed on Jul. 15, 2015 and entitled "Robotic Surgical Devices, Systems, and Related Methods"), U.S. patent application Ser. No. 13/573,849 (filed Oct. 9, 2012 and entitled "Robotic Surgical Devices, Systems, and Related Methods"), U.S. patent application Ser. No. 13/738,706 (filed Jan. 10, 2013 and entitled "Methods, Systems, and Devices for Surgical Access and Insertion"), U.S. patent application Ser. No. 13/833,605 (filed Mar. 15, 2013 and entitled "Robotic Surgical Devices, Systems, and Related Methods"), U.S. patent application Ser. No. 14/661,465 (filed Mar. 18, 2015 and entitled "Methods, Systems, and Devices for Surgical Access and Insertion"), U.S. Pat. No. 9,498,292 (issued on Nov. 22, 2016 and entitled "Single Site Robotic Devices and Related Systems and Methods"), U.S. patent application Ser. No. 15/357,663 (filed Nov. 21, 2016 and entitled "Single Site Robotic Devices and Related Systems and Methods"), U.S. Pat. No. 9,010,214 (issued on Apr. 21, 2015 and entitled "Local Control Robotic Surgical Devices and Related Methods"), U.S. patent application Ser. No. 14/656,109 (filed on Mar. 12, 2015 and entitled "Local Control Robotic Surgical Devices and Related Methods"), U.S. patent application Ser. No. 14/208,515 (filed Mar. 13, 2014 and entitled "Methods, Systems, and Devices Relating to Robotic Surgical Devices, End Effectors, and Controllers"), U.S. patent application Ser. No. 14/210,934 (filed Mar. 14, 2014 and entitled "Methods, Systems, and Devices Relating to Force Control Surgical Systems), U.S. patent application Ser. No. 14/212,686 (filed Mar. 14, 2014 and entitled "Robotic Surgical Devices, Systems, and Related Methods"), U.S. patent application Ser. No. 14/334,383 (filed Jul. 17, 2014 and entitled "Robotic Surgical Devices, Systems, and Related Methods"), U.S. patent application Ser. No. 14/853,477 (filed Sep. 14, 2015 and entitled "Quick-Release End Effectors and Related Systems and Methods"), U.S. patent application Ser. No. 14/938,667 (filed Nov. 11, 2015 and entitled "Robotic Device with Compact Joint Design and Related Systems and Methods"), U.S. patent application Ser. No. 15/227,813 (filed Aug. 3, 2016 and entitled "Robotic Surgical Devices, Systems, and Related Methods"), U.S. patent application Ser. No. 15/599,231 (filed May 18, 2017 and entitled "Robotic Surgical Devices, Systems, and Related Methods"), U.S. patent application Ser. No. 15/691,087 (filed Aug. 30, 2017 and entitled "Robotic Device with Compact Joint Design and an Additional Degree of Freedom and Related Systems and Methods"), U.S. Patent Application 62/425,149 (filed Nov. 22, 2016 and entitled "Improved Gross Positioning Device and Related Systems and Methods"), U.S. Patent Application 62/433,837 (filed Dec. 14, 2016 and entitled "Releasable Attachment Device for Coupling to Medical Devices and Related Systems and Methods"), and U.S. Pat. No. 7,492,116 (filed on Oct. 31, 2007 and entitled "Robot for Surgical Applications"), U.S. Pat. No. 7,772,796 (filed on Apr. 3, 2007 and entitled "Robot for Surgical Applications"), and U.S. Pat. No. 8,179,073 (issued May 15, 2011, and entitled "Robotic Devices with Agent Delivery Components and Related Methods"), all of which are hereby incorporated herein by reference in their entireties.

Thus, the various user controller 8 embodiments disclosed or contemplated herein can be used with any robotic surgical system to operate a robotic device or a component thereof, including such a device that is positioned in or through an incision into a target cavity or tissue of a patient. As such, the user utilizes her thumb and forefinger to manipulate the user controller 8, which thereby actuates the device or components thereof to perform a desired procedure.

Figure 2A:
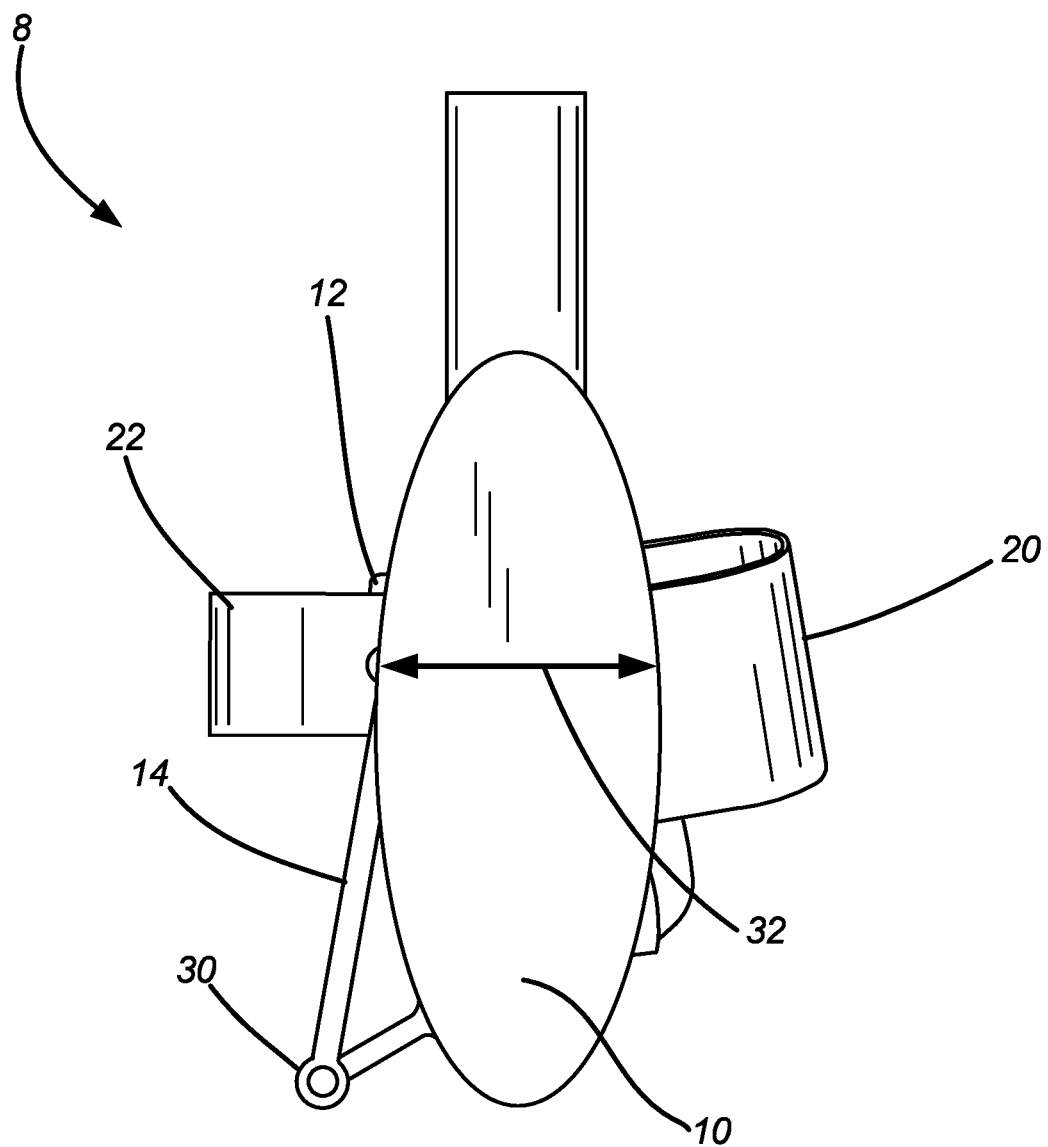
FIG. 2A is a top view of the known user input device of FIG. 1.
Figure 2B:
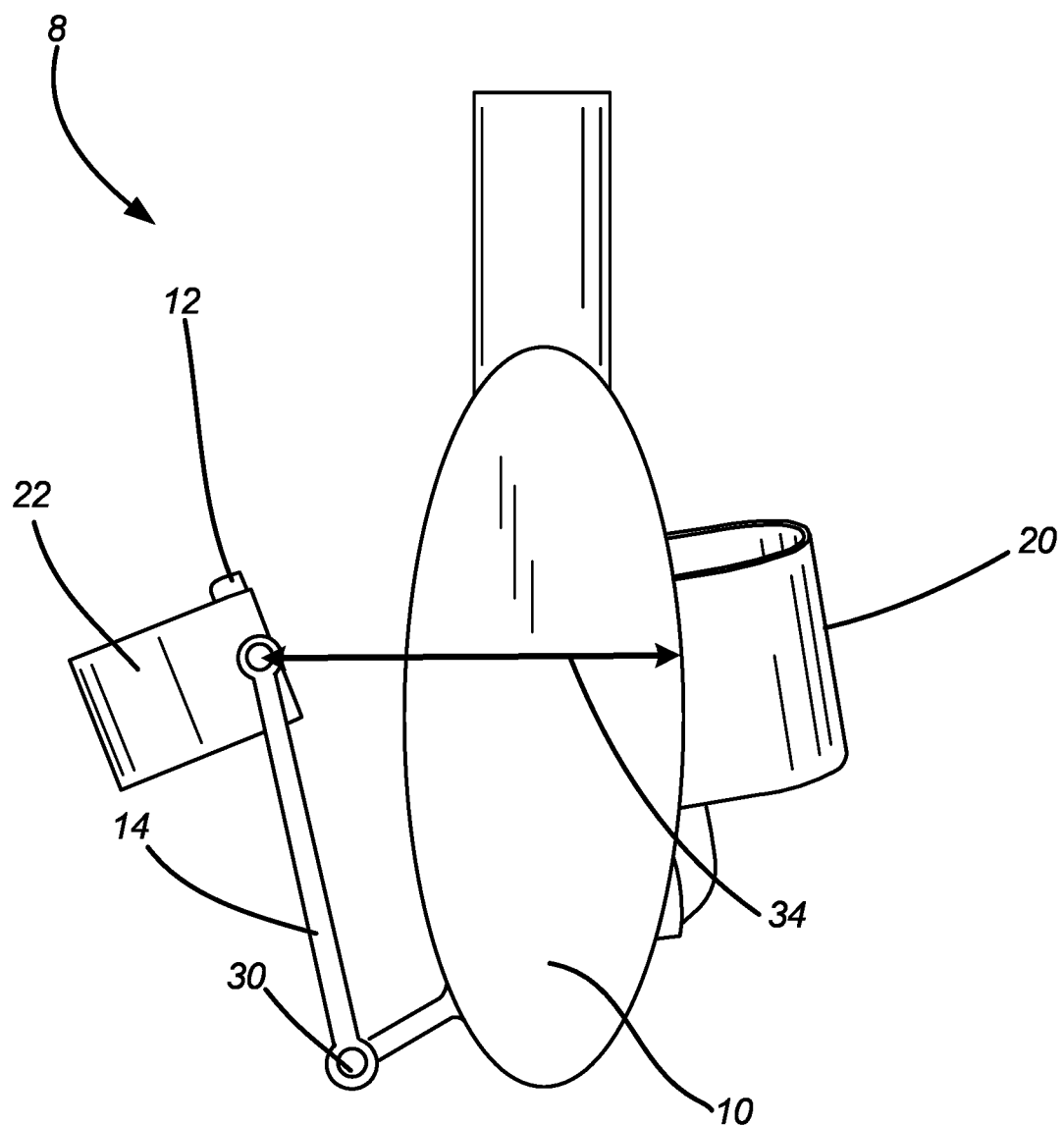
FIG. 2B is another top view of the known user input device of FIG. 1.
Figure 3:
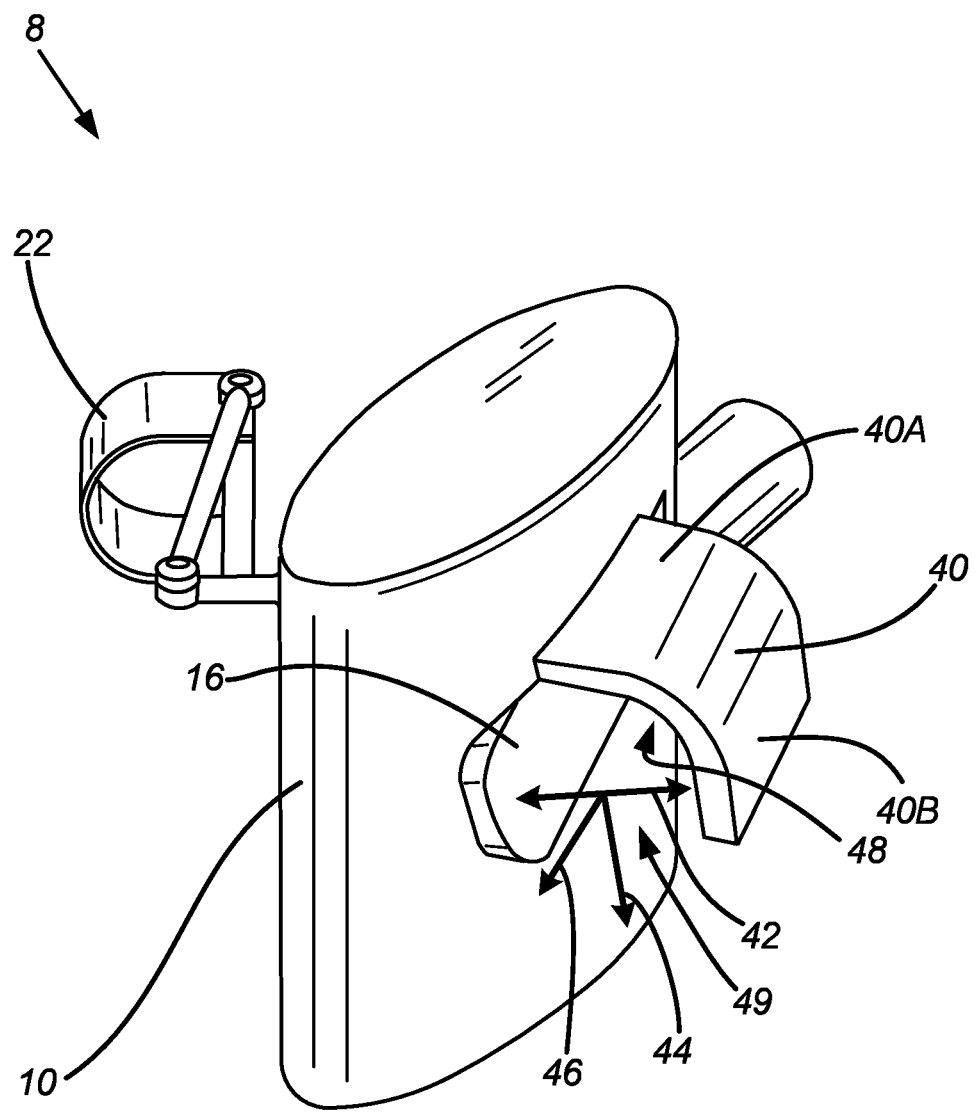
FIG. 3 is a perspective view of a user input device with a thumb sheath, according to one embodiment.

FIG. 3 depicts a user controller 8 according to one embodiment having a thumb sheath (also referred to as a "enclosure," "sleeve," or "shroud") 40, instead of a thumb restraint as discussed above in relation to FIGS. 1-2B. As used herein, "sheath," "enclosure," "sleeve," or "shroud" is intended to mean any structure that encloses the user's thumb on three sides while defining an opening on the fourth side through which the user can remove her thumb. The thumb sheath 40 surrounds the thumb on two sides, with the main body 10 restraining on a third side, leaving a single side open. More specifically, the sheath 40 has a first section 40A extending from the body 10 and a second section 40B extending from the first section 40A in a direction substantially transverse to the first section 40A, thereby enclosing two sides around the thumb opening 48 such that the thumb opening 48 is defined by the first section 40A, the second section 40B, and the thumb groove 16. Alternatively, the device 8 need not have a thumb groove—the body 10 can define the third side in such implementations. As a result, the thumb sheath 40 and the thumb groove 16 or body 10 further define an open side 49 as shown. In contrast, the known thumb restraint 20 discussed above operates in conjunction with the thumb groove 16 to entirely surround or enclose the thumb on four sides—the entire 360° around the thumb.

In one embodiment, the thumb sheath 40 can sufficiently constrains the user's thumb when it is positioned within the thumb opening 48 such that the thumb can be used to perform a "pinching motion" in conjunction with the forefinger to cause the forefinger restraint 22 to move away from or closer to the body 10 in the directions represented by arrow 42. As such, the thumb sheath 40 can operate in a fashion similar to the known thumb restraint 20 discussed above. In contrast to that restraint 20, however, the sheath 40 also allows two methods of egress for the thumb. That is, the user's thumb can not only be retracted proximally in the direction represented by arrow 46 in the same fashion as possible with the known thumb restraint 20, but can also be moved out of the thumb opening 48 in the direction represented by arrow 44 through the open side 49. As can be seen in FIG. 3, the two directions of potential egress are normal to the direction of pinching (represented by arrow 42) and each other. As such, this configuration of the sheath 40 allows for both fine control of pinching motion while enabling the user to disengage from the device 8 by removing her thumb in a controlled and simple manner.

To clarify, the term "user controller" as used herein will refer to the various embodiments of a user input device to be manipulated by a user to provide input to and thereby operate some portion of a robotic system. In contrast, the term "system controller" will refer to any processor, computer or other system controller component (such as a microprocessor or the like) that can be used to operate a system.

Figure 4:
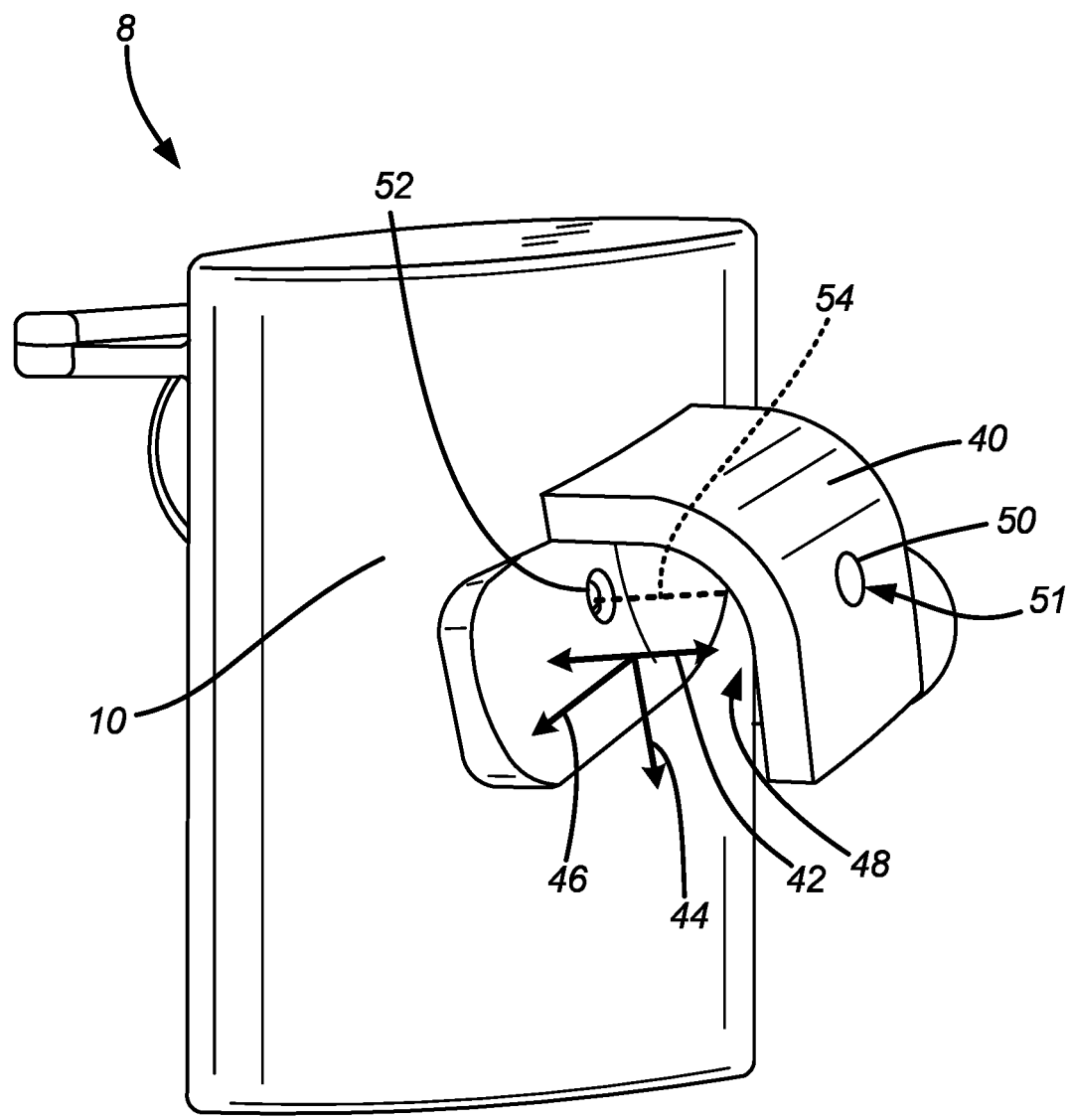
FIG. 4 is a perspective view of a user input device with a thumb sheath and a light-based sensor, according to one embodiment.

FIG. 4 depicts a further implementation of a user controller 8 having a sensor 51 configured to detect the presence of the user's thumb. It is understood that this embodiment of the controller 8 has a thumb sheath 40 substantially similar to the sheath 40 described above, including the features and benefits as described. Further, in this exemplary implementation, a user presence sensor 51 is incorporated into the sheath 40. The device 8 has a matched light emitter 50 disposed on the sheath 40 and a receiver 52 disposed on the body 10. Alternatively, the emitter can be on the body 10 and the receiver can be on the sheath 40. In a further alternative, two or more such sensors can be incorporated into the device 8. The emitter 50 and receiver 52 are positioned in a manner which generally aligns the path of light 54 transmitted by the emitter 50 with the direction of motion of the pinching motion as represented by arrow 42. In use, the emitter 50 and receiver 52 are placed such that when the user's thumb is not present, light (visible or otherwise) from the emitter 50 reaches the receiver 52. In contrast, when the user's thumb is present within the thumb opening 48, the path of the light 54 is blocked. The absence of this signal can then be used as an indicator of user presence (that is, the presence of the user's thumb within the thumb opening 48), thereby indicating that the user is grasping the user controller 8. Once the light path is blocked by the user's thumb, restoration of this signal, an indicator of user absence, is achieved by retracting the thumb in either of two directions as represented by arrows 44 and 46, which are normal to the direction of pinching represented by arrow 42 and the path of light 54 (as discussed above). This configuration of sheath 40 and sensor 51 allows for motion of the thumb in the direction of pinching (as represented by arrow 42) without allowing light to pass. This allows for the sheath 40 to be sufficiently loose such that egress is easily achieved. That is, the size of the thumb opening 48 in relation to the user's thumb does not impact the ability of the sensor 51 to detect the presence therein or the ability of the user to utilize the sheath 40 to allow the user to utilize the pinching motion to move the forefinger restraint as discussed above.

Alternatively, any known sensor or sensor technology can be used with the user controller 8 to detect the presence (and absence) of the user's thumb within the sheath 40.

The sensor 51 allows for the user controller 8 (and the system to which the controller 8 is coupled) to utilize the information about the presence or absence of the user's thumb to activate or deactivate mechanical support of the user controller 8. That is, the sensor 51 can be configured to transmit a "presence" signal to the system controller (not shown) of the system (not shown) when the thumb is inserted into the sheath 40 such that the system controller deactivates any mechanical support of the user controller 8. Similarly, the sensor 51 can also be configured to transmit an "absence" signal to the system controller (not shown) when the thumb is retracted from the sheath 40 such that the system controller activates mechanical support of the user controller 8, thereby preventing gravity from causing the user controller 8 from moving in an undesirable fashion that causes the controlled robotic device to also move in an undesirable fashion.

Figure 5:
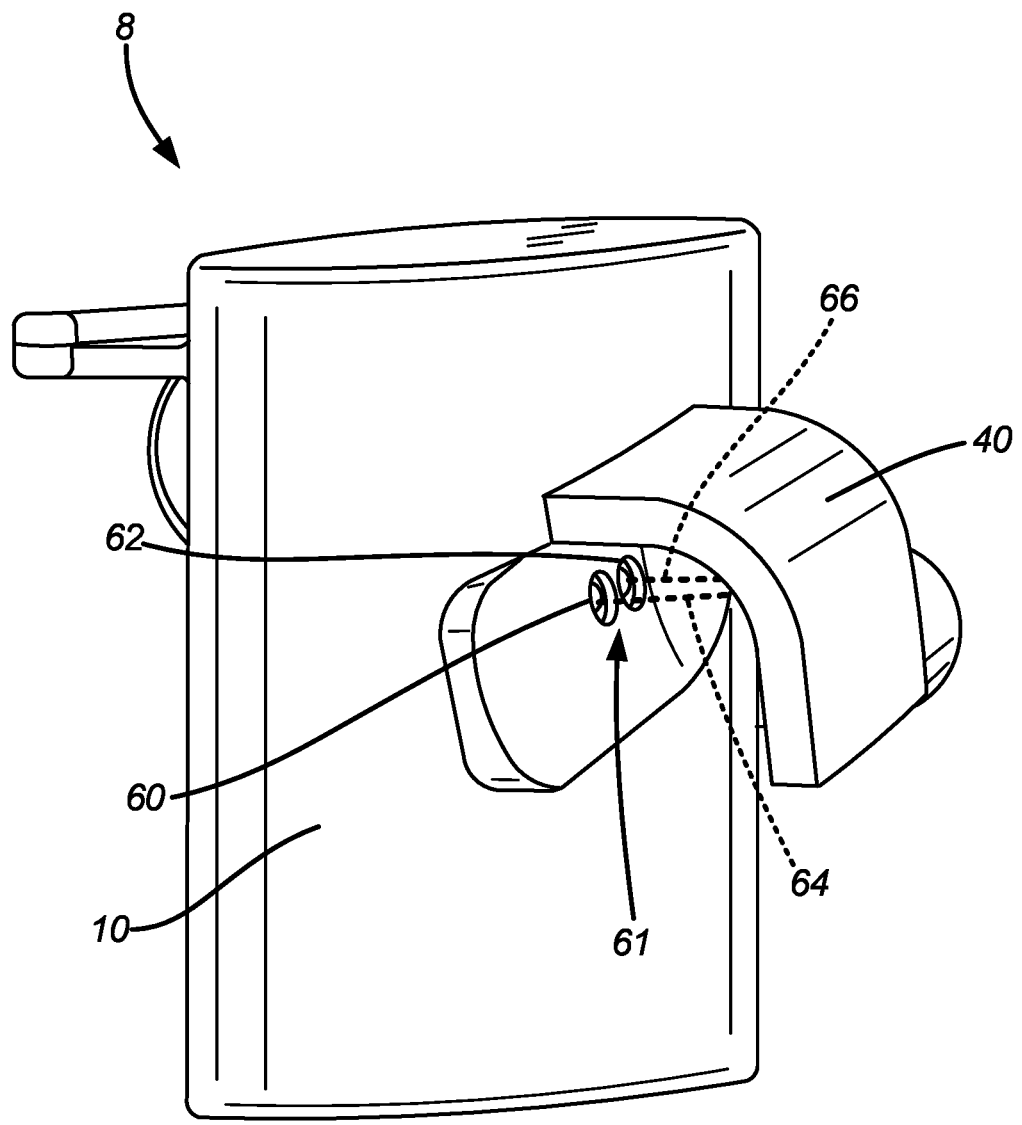
FIG. 5 is a perspective view of a user input device with a thumb sheath and another light-based sensor, according to a further embodiment.

FIG. 5 depicts an alternative embodiment of a user controller 8 having a reflected light sensor 61. That is, the user controller 8 has an emitter 60 and a receiver 62 that are both embedded in the main body 10 as shown such that the emitted light 64 from the emitter 60 returns to the receiver 62 as reflected light 66 by the nearest occlusion. In this configuration, the presence of the user's thumb within the sheath 40 provides a much shorter path than the sheath 40 and thus a corresponding stronger return signal than would be detected in the absence of the thumb. This signal can then be thresholded to determine the binary presence/absence of the user's thumb. That is, a predetermined threshold can be established above which it is understood that a user's thumb is present in the sheath 40 such that a presence signal is transmitted to the system controller (not shown). In one implementation, it is understood that this embodiment has substantially the same features, modes of egress, and advantages, including insensitivity to motion in the direction of pinching motion, as the previously described embodiments.

Figure 6:
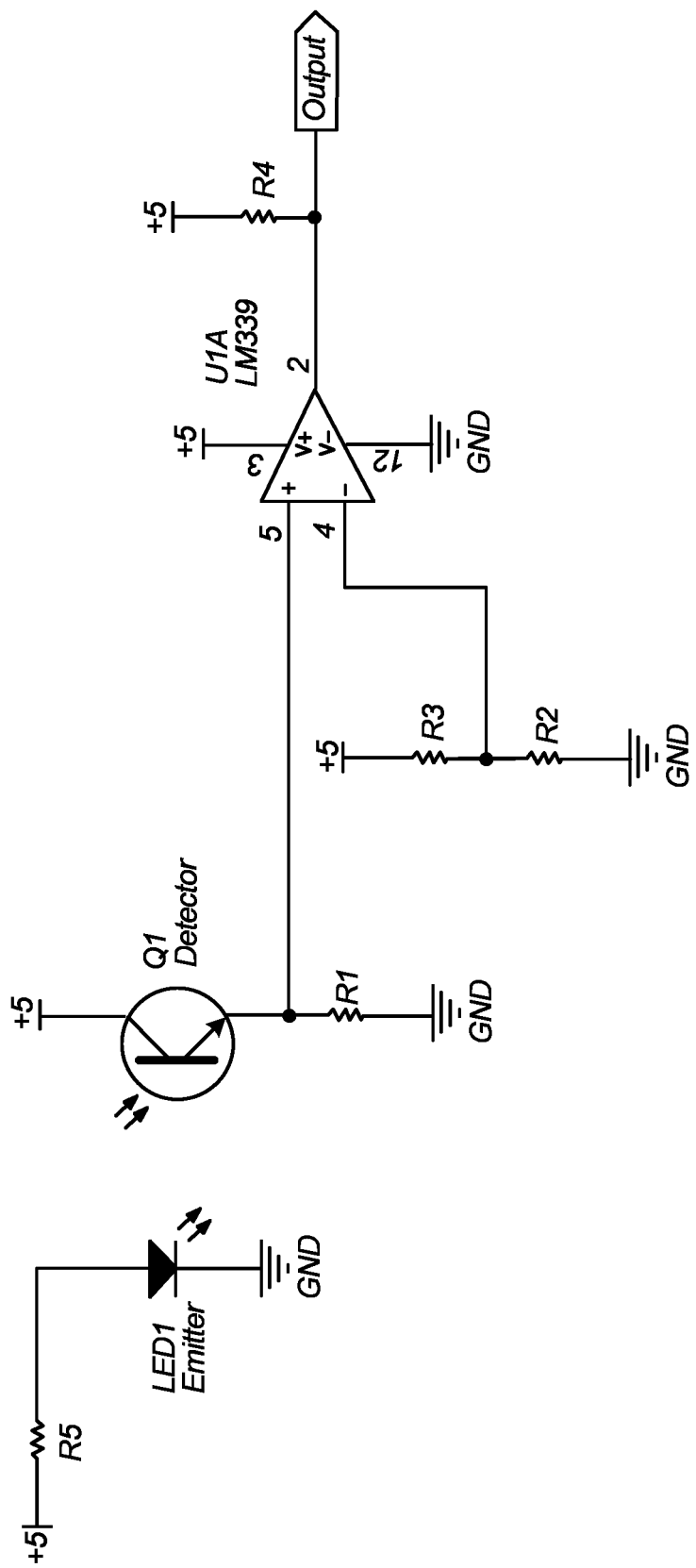
FIG. 6 is a schematic depiction of a known circuit configuration for use with a light-based sensor, according to one embodiment.

FIG. 6 depicts an exemplary known circuit for use in conjunction with a sensor such as either of the sensors 51, 61 discussed above with respect to FIGS. 4 and 5 for detecting the presence of a user's thumb within the sheath 40. In this embodiment, one or more pairs of infrared (IR) emitters and detectors are provided that are similar to those described in FIG. 4 or FIG. 5. The presence of the user's thumb blocks the IR light from the emitter from reaching the detector, changing the output state of the circuit. Each emitter/detector pair described uses the circuit in FIG. 6 to detect presence. When the user's thumb is absent from the device, phototransistor Q1 receives IR light from LED1. This turns the transistor on, causing a current to flow through resistor R1, and a non-zero voltage to appear on the non-inverting input (pin 5) of the comparator U1. If this voltage is higher than the inverting input of U1, set by the voltage divider of R2 and R3, the output of the comparator is switched on, lowering the output voltage to 0. When the detector Q1 is blocked, the transistor is off, and the output of the circuit is 5 volts. Alternatively, any known circuit or circuit configuration can be used for this purpose.

Figure 7:
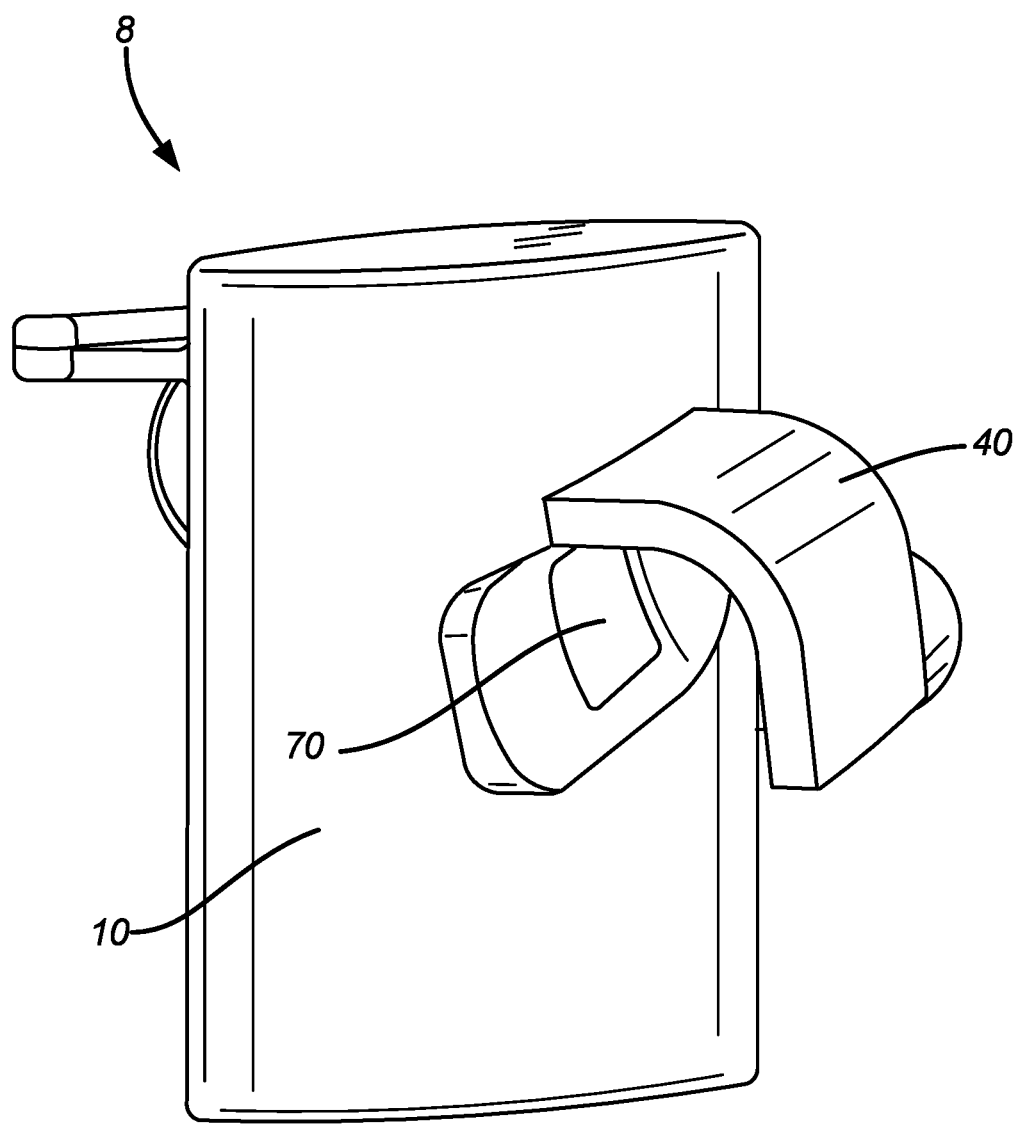
FIG. 7 is a perspective view of a user input device with a thumb sheath and a capacitive sensor, according to one embodiment.

FIG. 7 depicts a further embodiment of a sensor 70 for use in a user controller 8. In this specific implementation, instead of a light-based technology, the sensor 70 is a known capacitive sensor 70 positioned in the main body 10 as shown. The capacitive sensor 70 functions as a known capacitive sensor 70 operates to detect the presence of the user's thumb within the sheath 40. According to one embodiment, it is understood that this embodiment has substantially the same features, modes of egress, and advantages, including insensitivity to motion in the direction of pinching motion, as the previously described embodiments.

Figure 8:
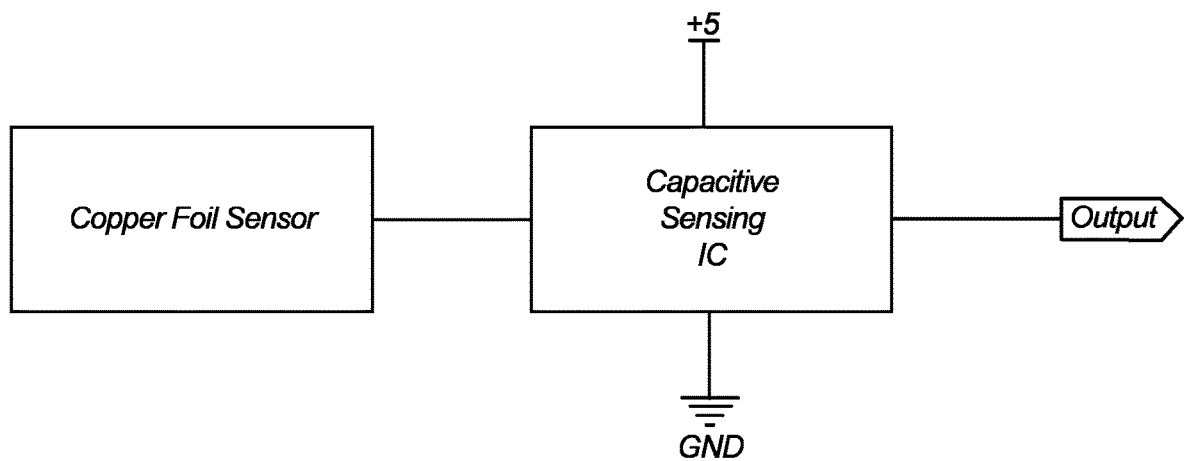
FIG. 8 is a schematic depiction of a known circuit configuration for use with a capacitive sensor, according to one embodiment.

FIG. 8 depicts an exemplary known circuit for use in conjunction with a capacitive sensor such as the sensor 70 discussed above with respect to FIG. 7 for detecting the presence of a user's thumb within the sheath 40, according to another implementation. One or more capacitive sensors are placed on the inner surface of the thumb sheath, such as the sensor 70 in FIG. 7. In use, when the user's thumb is placed in the sheath 40, the change in capacitance changes the output state of the circuit. Alternatively, any known circuit or circuit configuration that operates in conjunction with a capacitive sensor can be used for this purpose.

Figure 12:
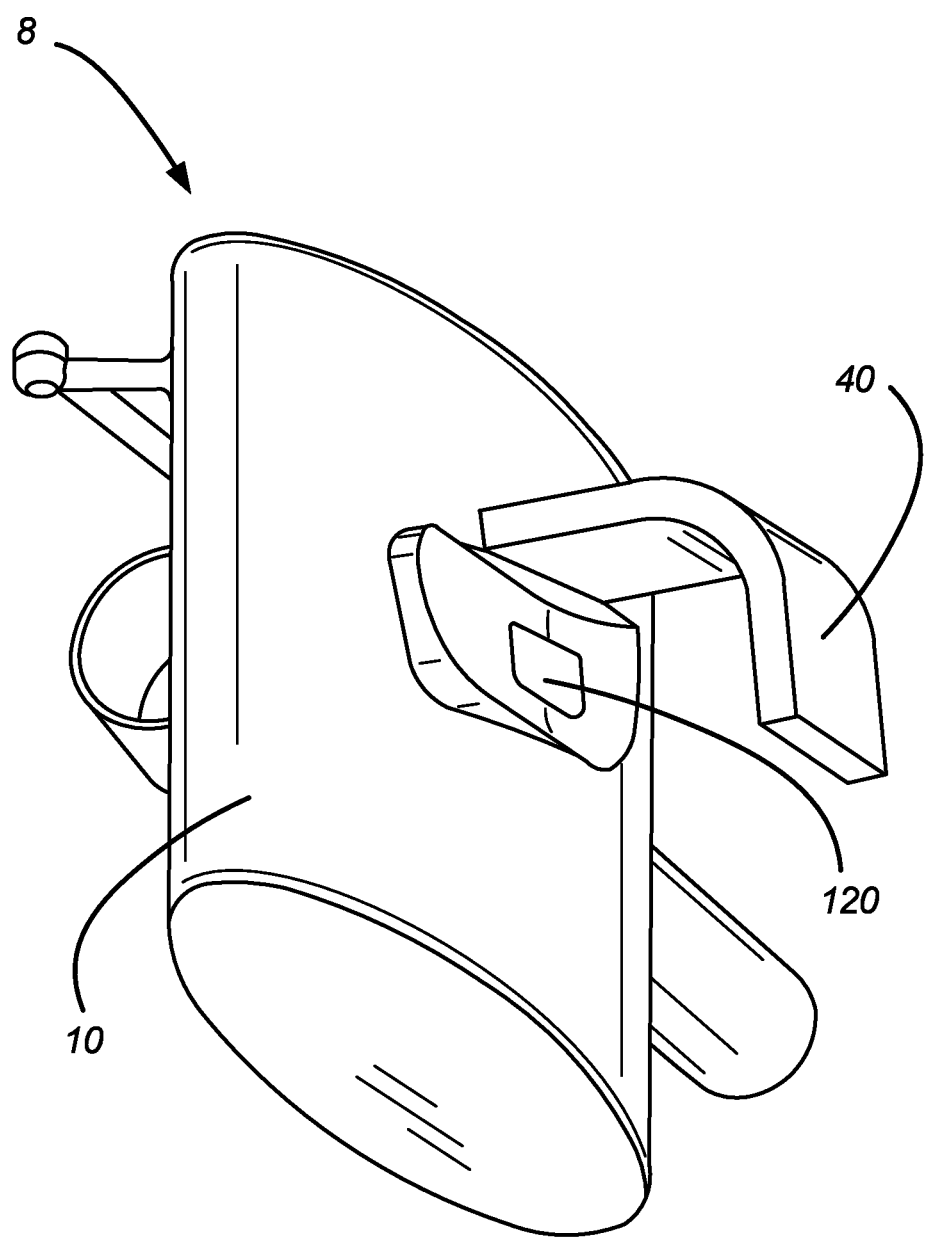
FIG. 12 is a perspective view of a user input device with a thumb sheath and a mechanical sensor, according to one embodiment.

FIG. 12 depicts a further embodiment of a sensor 120 for use in a user controller 8. In this specific implementation, instead of a light- or capacitive-based technology, the sensor 120 is a known mechanical sensor 120 positioned in the main body 10 as shown. The mechanical sensor 120 functions as a known mechanical sensor 120 operates to detect the presence of the user's thumb within the sheath 40. For example, the mechanical sensor 120 can be actuated by the user's thumb depressing the sensor 120, thereby indicating that the thumb is present within the sheath 40. According to one embodiment, it is understood that this embodiment has substantially the same features, modes of egress, and advantages, including insensitivity to motion in the direction of pinching motion, as the previously described embodiments.

Figure 9:
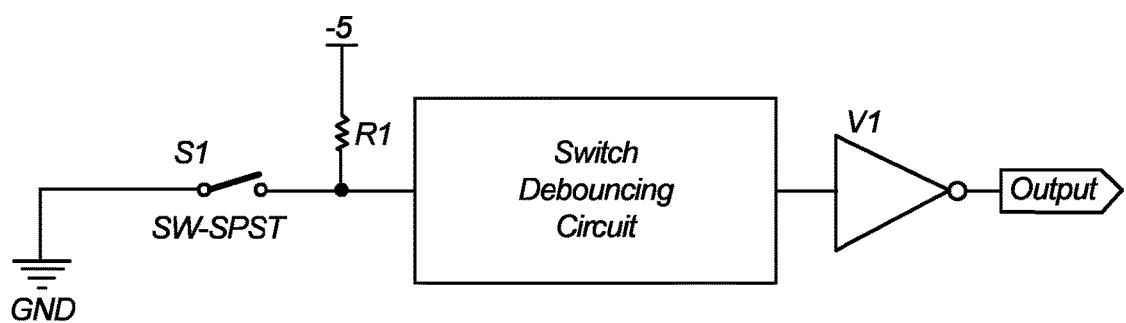
FIG. 9 is a schematic depiction of a known circuit configuration for use with a mechanical sensor, according to one embodiment.

FIG. 9 depicts an exemplary known circuit for use in conjunction with a mechanical sensor such as sensor 120 discussed above with respect to FIG. 12 for detecting the presence of a user's thumb within the sheath 40, according to a further embodiment. In this embodiment, a mechanical switch (such as switch 120) is placed inside of the thumb sheath 40. In use, when the user's thumb is in place, the switch is actuated and the output state of the circuit changes. When the user's thumb is not in the sheath, the switch is open, and the output of the switch is pulled up to 5 volts. V1 inverts this signal to a 0 volt output. When the thumb is placed in the sheath, the switch is depressed, which changes the output of the circuit to 5 V. The switch debouncing circuitry is a circuit which filters out short duration transitions of the output when the mechanical switch is engaged and disengaged. Alternatively, any known circuit or circuit configuration that operates in conjunction with a mechanical sensor can be used for this purpose.

Figure 10:
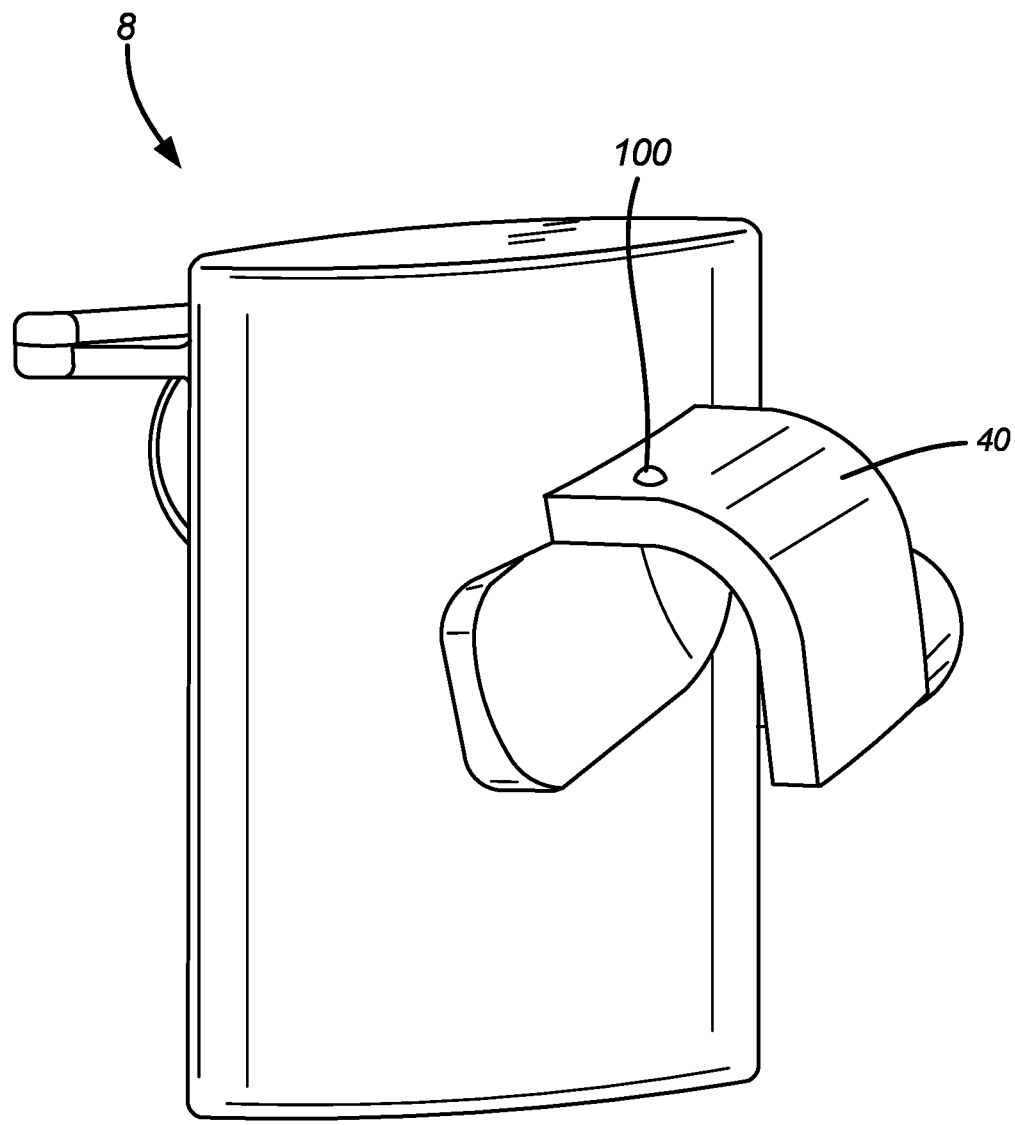
FIG. 10 is a perspective view of a user input device with a thumb sheath and a sensory signal, according to one embodiment.

FIG. 10 depicts a user controller 8 having a user sensory feedback signal component 100, according to one embodiment. That is, this specific implementation has a signal component 100 that provides some type of sensory feedback to the user about whether the user's thumb is positioned within the sheath 40. In the specific embodiment depicted in FIG. 10, the feedback signal component 100 is a visual feedback component 100 in the form of an LED 100 that is disposed on the thumb sheath 40. Alternatively, any form of sensory feedback signal can be used. This feedback component 100 provides feedback to the user regarding whether the system (not shown) detects the presence of the user's thumb within the sheath 40. Feedback may be provided by multiple LEDs, auditory, or other visual signals. In use, according to this embodiment, the LED 100 would illuminate if the user's thumb is detected, thereby indicating that the thumb is positioned within the sheath 40. It is understood that the user controller 8 with the user feedback signal component 100 can have any of the various sensor components disclosed or contemplated herein. In addition, it is understood that the user feedback signal component 100 can be incorporated into any other embodiment disclosed or contemplated herein.

Figure 11A:
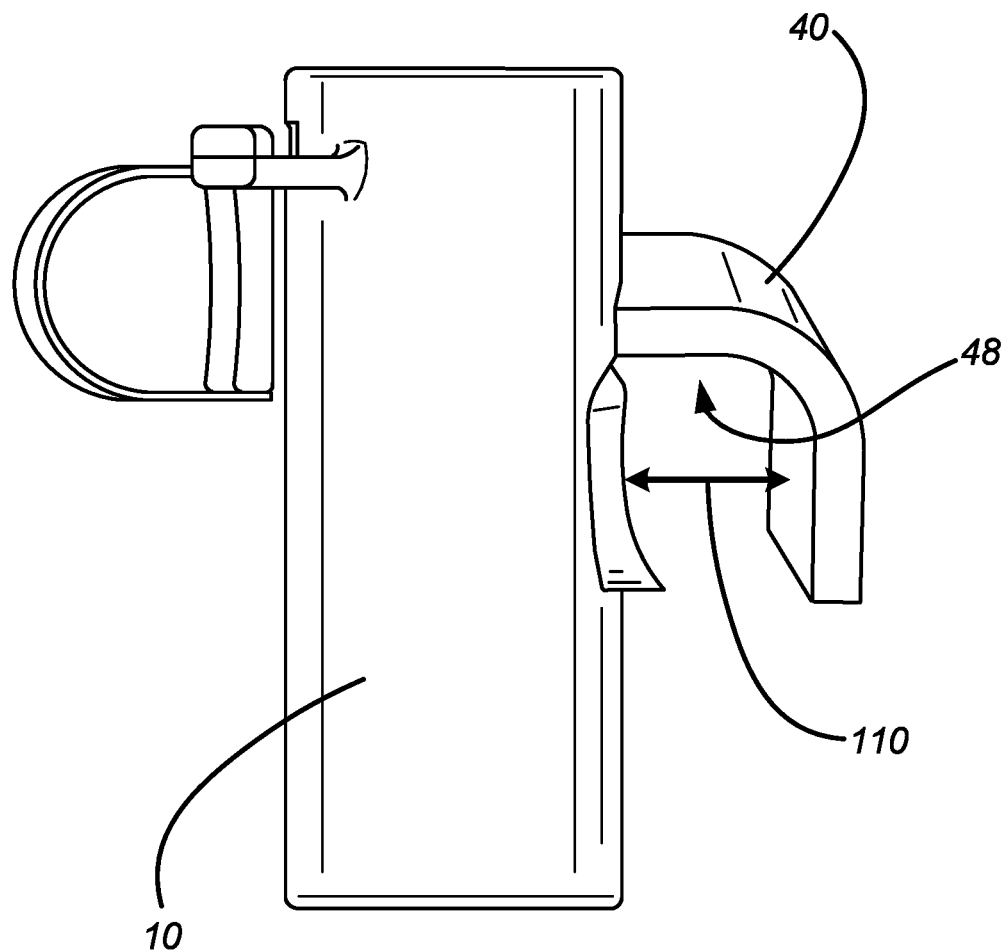
FIG. 11A is a perspective view of a user input device with an adjustable thumb sheath in a retracted position, according to a further embodiment.
Figure 11B:
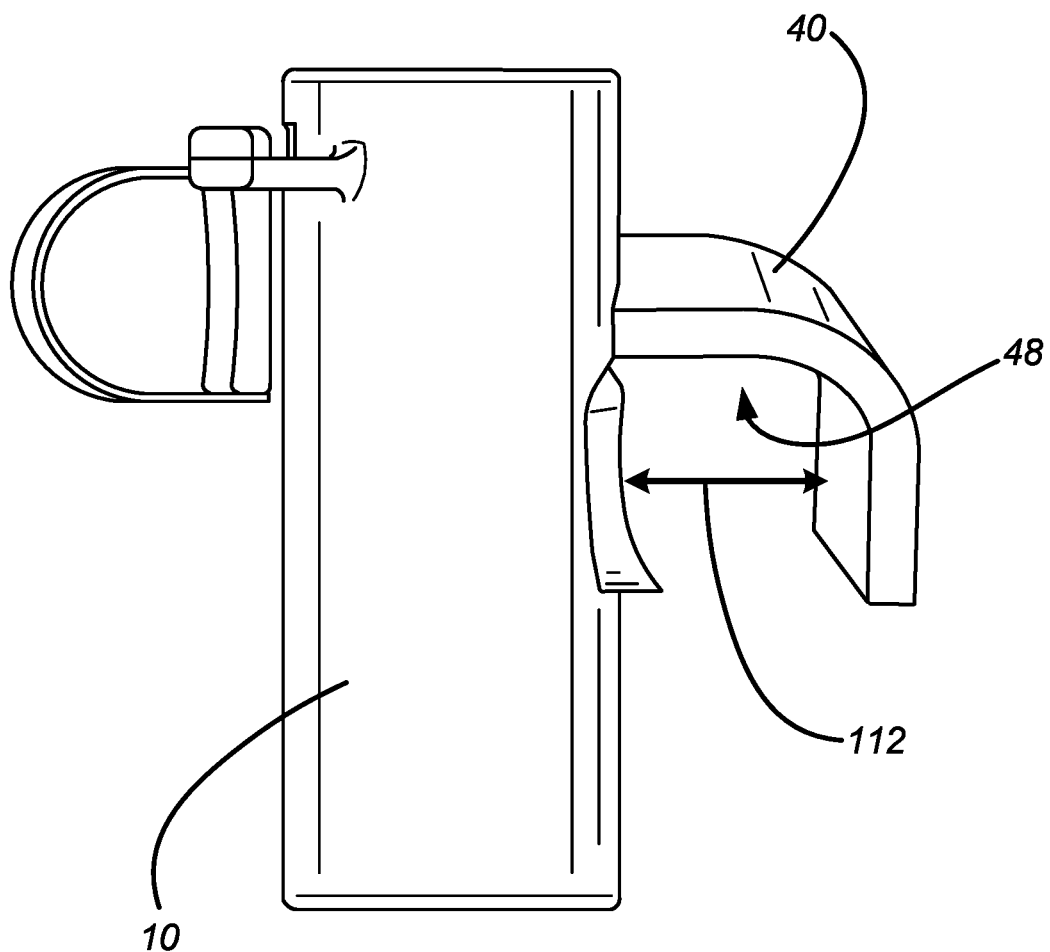
FIG. 11B is a perspective view of a user input device with an adjustable thumb sheath in an extended position, according to a further embodiment.

FIGS. 11A and 11B depict an adjustable sheath 40, according to one embodiment. More specifically, the sheath 40 in this specific implementation can move between a retracted position as shown in FIG. 11A and an extended position as shown in FIG. 11B. As such, the sheath 40 can be adjusted to be positioned with respect to the main body 10 in the retracted positioned in which the thumb opening 48 has a minimum width represented by arrow 110 (as shown in FIG. 11A) or can be extended out away from the body 10 up to the extended position in which the thumb opening 48 has a maximum width represented by arrow 112 (as shown in FIG. 11B). This adjustability enables the sheath 40 to conform to a wide array of user thumb sizes while supplying sufficient control authority to the user while still enabling the user to disengage in a controlled manner. It is further understood that the user controller 8 with the adjustable sheath 40 can have any of the various sensor or sensory feedback components disclosed or contemplated herein. In addition, it is understood that the adjustable sheath 40 can be incorporated into any other embodiment disclosed or contemplated herein.

Although the present invention has been described with reference to preferred embodiments, persons skilled in the art will recognize that changes may be made in form and detail without departing from the spirit and scope of the invention.

What is claimed is:

1. A user controller comprising:
   (a) a controller body;
   (b) a forefinger restraint operably coupled to the controller body such that the forefinger restraint is movable away from or closer to the controller body via a pinching motion of a user;
   (c) a thumb sheath coupled to the controller body, the thumb sheath and the controller body defining a thumb opening and a side opening, the thumb opening defined by a side of the controller body, a first section of the thumb sheath extending from the controller body, and a second section of the thumb sheath extending from the first section of the thumb sheath, and the side opening defined by the second sheath section and the controller body; and
   (d) a thumb presence sensor disposed within the thumb sheath, wherein the thumb presence sensor is configured to detect a presence of a thumb of the user disposed in the thumb opening, including during the pinching motion.

2. The user controller of claim 1, wherein the thumb sheath and the controller body do not form a 360° enclosure around the thumb opening.

3. The user controller of claim 1, wherein the thumb presence sensor comprises a light sensor disposed within the thumb opening.

4. The user controller of claim 1, wherein the thumb presence sensor comprises a light emitter disposed on an inner wall of the thumb sheath and a light receiver disposed on the controller body, wherein the light receiver is positioned to receive light transmitted by the light emitter.

5. The user controller of claim 1, wherein the thumb presence sensor comprises a light emitter disposed on the controller body and a light receiver disposed on an inner wall of the thumb sheath, wherein the light receiver is positioned to receive light transmitted by the light emitter.

6. The user controller of claim 1, wherein the thumb presence sensor comprises a light emitter and a light receiver, wherein the light emitter and light receiver are disposed on the controller body.

7. The user controller of claim 1, wherein the thumb presence sensor comprises a capacitive sensor disposed on the controller body within the thumb sheath.

8. The user controller of claim 1, wherein the thumb presence sensor comprises a mechanical sensor disposed on the controller body within the thumb sheath.

9. The user controller of claim 1, wherein the thumb sheath is adjustable between a retracted position and an extended position.

10. The user controller of claim 1, wherein the thumb presence sensor comprises a feedback signal component disposed on an outer surface of the thumb sheath, wherein the feedback signal component is visible to a user.

11. The user controller of claim 1, wherein a user's thumb is removable from the thumb sheath via the thumb opening or the side opening.

12. A robotic surgical system comprising:
   (a) a system controller;

(b) a robotic surgical device operably coupled to the system controller; and
(c) a user controller operably coupled to the system controller, the user controller comprising:
(i) a controller body;
(ii) a forefinger restraint operably coupled to the controller body such that the forefinger restraint is movable away from or closer to the controller body via a pinching motion of a user;
(iii) a thumb sheath coupled to the controller body, wherein the thumb sheath and the controller body define a thumb opening and a side opening, and wherein the thumb sheath comprises:
(A) a first sheath section extending from the controller body, the first sheath section defining a first wall of the thumb opening;
(B) a second sheath section extending from the first sheath second, the second sheath section defining a second wall of the thumb opening; and
(C) a third wall of the thumb opening defined by the controller body;
and
(iv) a thumb presence sensor disposed within the thumb sheath, wherein the thumb presence sensor is configured to detect a presence of a thumb of the user disposed in the thumb opening, including during the pinching motion.

13. The robotic surgical system of claim 12, wherein the side opening is defined between the second wall and the third wall.

14. The robotic surgical system of claim 12, wherein the thumb sheath does not form a 360° enclosure around the thumb opening.

15. The robotic surgical system of claim 12, wherein the thumb presence sensor comprises a light sensor, a capacitive sensor, or a mechanical sensor.

16. The robotic surgical system of claim 12, wherein the thumb sheath is adjustable between a retracted position and an extended position.

17. The robotic surgical system of claim 12, further comprising a feedback signal component disposed on an outer surface of the thumb sheath, wherein the feedback signal component is visible to a user.

18. The robotic surgical system of claim 12, wherein a user's thumb is removable from the thumb sheath via the thumb opening or the side opening.

19. A user controller comprising:
(a) a controller body;
(b) a forefinger restraint operably coupled to the controller body such that the forefinger restraint is movable away from or closer to the controller body via a pinching motion of a user;
(c) a thumb sheath coupled to the controller body, the thumb sheath being adjustable between a retracted position and an extended position, the thumb sheath comprising:
(i) a first sheath section extending from the controller body;
(ii) a second sheath section extending from the first sheath section, wherein the second sheath section is substantially transverse to the first sheath section;
(iii) a thumb opening defined by the first sheath section, the second sheath section, and the controller body; and
(iv) an open side defined by the second sheath section and the controller body;
and
(d) a thumb presence sensor disposed within the thumb sheath, wherein the thumb presence sensor is configured to detect a presence of a thumb of the user disposed in the thumb opening, including during the pinching motion.

20. The user controller of claim 19, wherein the first sheath section, the second sheath section, and the controller body do not form a 360° enclosure around the thumb opening.

21. The user controller of claim 19, wherein the thumb presence sensor comprises a light emitter and a light receiver, wherein the light receiver is positioned to receive light transmitted by the light emitter.

22. The user controller of claim 19, wherein a user's thumb is removable from the thumb sheath via the thumb opening or the open side.

* * * * *